(12) United States Patent
de Lanerolle et al.

(10) Patent No.: US 6,831,156 B2
(45) Date of Patent: Dec. 14, 2004

(54) NUCLEAR MYOSIN I βWITH A 16 AMINO ACID N-TERMINAL EXTENSION

(76) Inventors: Primal de Lanerolle, 823 Fair Oaks, Oak Park, IL (US) 60302; Grzegorz Nowak, 6007 N. Sheridan, Apt. 13E, Chicago, IL (US) 60660; Lidija Pestic-Dragovich, 1431 E. Paseo del Zorro, Tucson, AZ (US) 85718; Ljuba Stojilkovic, 440 Atwater Ave., Elmhurst, IL (US) 60126; Pavel Hozak, Vestec 307, 252 42 Jesenice u Prahy (CZ)

( * ) Notice: Subject to any disclaimer, the term of this patent is extended or adjusted under 35 U.S.C. 154(b) by 0 days.

(21) Appl. No.: 09/893,371

(22) Filed: Jun. 27, 2001

(65) Prior Publication Data

US 2003/0017511 A1 Jan. 23, 2003

Related U.S. Application Data

(60) Provisional application No. 60/214,944, filed on Jun. 29, 2000.

(51) Int. Cl.$^7$ .......................... C07K 14/47; C07K 14/00
(52) U.S. Cl. ....................... 530/358; 530/350; 530/300; 530/326
(58) Field of Search ................................ 530/350, 358, 530/300, 326

(56) References Cited

PUBLICATIONS

Barylko et al., "Purification and Characterization of a Mammalian Myosin I," *Proc. Natl. Acad. Sci. USA* 89:490–494, (1992).
Berezney et al., "Nuclear Protein Matrix: Association with Newly Synthesized DNA," *Science* 189:291–293, (1975).
Cook, P.R., "The Nucleoskeleton and the Topology of Replication," *Cell* 66:627–635, (1991).
Cook, P.R., "The Organization of Replication and Transcription," *Science* 284:1790–1795, (1999).
Crozet et al., "Cloning of the Genes Encoding Two Murine and Human Cochlear Unconventional Type I Myosins," *Genomics* 40:332–341 (1997).
de Lanerolle et al., "Myosin Phosphorylation During Contraction and Relaxation of Tracheal Smooth Muscle," *The Journal of Biological Chemistry* 255(20):9993–10000, (1980).
Hamilton et al., "The Vibrator Mutation Causes Neurodegeneration via Reduced Expression of PITPα: Positional Complementation Cloning and Extragenic Suppression," *Neuron* 18:711–722, (1997).
Hasson et al., "Mapping of Unconventional Myosins in Mouse and Human," *Genomics* 36:431–439, (1996).
Hunt et al., "Characterization of Peptides Bound to the Class I MHC Molecule HLA–A2.1 by Mass Spectrometry," *Science* 255:1261–1263, (1992).
Lavole et al., "Heat Shock–Induced Alterations in Phosphorylation of the Largest Subunit of RNA Polymerase II as Revealed by Monoclonal Antibodies CC–3 and MPM–2," *Biochem. Cell Biol.* 77:367–374, (1999).
Mermall et al., "Unconventional Myosins in Cell Movement, Membrane Traffic, and Signal Transduction," *Science* 279:527–533, (1998).
Nguyen et al., "In Vivo Degradation of RNA Polymerase II Largest Subunit Triggered by α–amanitin," *Nucleic Acids Research* 24(15):2924–2929, (1996).
Nowak et al., "Evidence for the Presence of Myosin I in the Nucleus," *The Journal of Biological Chemistry* 272(27):17176–17181, (1997).
Pestic–Dragovich et al., "A Myosin I Isoform in the Nucleus," *Science* 290:337–341, (2000).
Pollard et al., "Acanthamoeba Myosin," *The Journal of Biological Chemistry* 248(13):4682–4690, (1973).
Rando et al., "Searching for a Function for Nuclear Actin," *Cell Biology* 10:92–97, (2000).
Ruppert et al., "Localization of the Rat Myosin I Molecules myr 1 and myr 2 and in vivo Targeting of Their Tail Domains," *Jounral of Cell Science* 108:3775–3786, (1995).
Scheer et al., "Microinjection of Actin–Binding Proteins and Actin Antibodies Demonstrates Involvement of Nuclear Actin in Transcription of Lampbrush Chromosomes," *Cell* 39:111–122, (1984).
Toulme, J., "New Candidates for True Antisense," *Nature Biotechnology* 19:17–18, (2001).
Yin et al., "Transcription Against an Applied Force," *Science* 270:1653–1657, (1995).

*Primary Examiner*—Larry R. Helms
*Assistant Examiner*—Misook Yu
(74) *Attorney, Agent, or Firm*—Kenneth Barovsky (57) ABSTRACT

The present invention relates to a molecular motor actin binding protein, in particular, to Nuclear Myosin Iβ (NMIβ) containing a 16 amino acid N-terminal extension involved in transcription. More particularly, this invention is directed to a molecule with oligonucleotide sequence coding for a protein nuclear Myosin Iβ (NMIβ) containing a 16 amino acid N-terminal extension that co-localizes with, and forms functional complexes with, RNA polymerase II. This invention is also directed to polyclonal and monoclonal antibodies to the 16 amino acid N-terminal extension that block in vitro RNA synthesis. This invention is also directed to administration to a cell of polyclonal or monoclonal antibodies to the NMIβ 16 amino acid N-terminal extension sequence or to an epitope within that sequence to inhibit transcription. Other inhibitors are also suitable. This invention may be used to treat illness through targeted inhibition of cell proliferation.

3 Claims, 6 Drawing Sheets

FIG. 1

| | | | |
|---|---|---|---|
| mryrasalgs | dgvrvtm*esa | ltardrvgvq | dfvllenfts |
| eaafienlrr | rfrenliyty | igpvlvsvnp | yrdlqiysrq |
| hmeryrgvsf | yevpphlfav | adtvyralrt | errdqavmis |
| [gesgagkt]ea | tkrllqfyae | tcpapergga | vrdrllqsnp |
| vleafgnakt | lmdnssrfg | kymdvqfdfk | gapvgghils |
| ylleksrvvh | qnhgemfhv | fyqlleggee | etlrrlgler |
| npqsylylvk | gqcakvssin | dksdwkvmrk | alsvidfted |
| evedllsiva | svlhlgnihf | aadedsnaqv | ttenqlkylt |
| rllgvegttl | realthrkii | akgeellspl | nleqaayard |
| alakavysrt | ftwlvrkinr | slaskdaesp | swrsttvlgl |
| ldiygfevfq | hnsfeqfcin | ycneklqqlf | ieltlkseqe |
| eyeaegiawe | pvqyfnnkii | cdlveekfkg | iisildeecl |
| rpgeatdltf | lekledtvkp | hphflthkla | dqktrksldr |
| gefrllhyag | evtysvtgfl | dknndllfrn | lketmcssmn |
| pimaqcfdks | elsdkk rpet | vatqfkmsll | qlveilrske |
| payircikpn | dakqpgrfde | vlirhqvkyl | glmenlrvrr |
| agfayrrkye | aflqrykslc | petwpmwagr | pqdgvavlvr |
| hlgykpeeyk | mgrtkifirf | pktlfateds | levrrqslat |
| kiqaawrgfh | wrqkflrvkr | saiciqswwr | gtlgrrkaakr |
| kwaaqtirr | lirgfilrhs | pr cpenaffl | dhvrasflln |
| lrrqlpmvl | dtswptpppa | lreasellrel | cmknmvwky |
| crsispewkq | qlqqkavase | ifkgkkdnyp | qsvprlfist |
| rlgteeispr | vlqslgsepi | qyavpvvkyd | rkgykprprq |
| llltpsavvi | vedakvkqri | dyanltgisv | sslsdslfvl |
| hvqrednkqk | gdvvlqsdhv | ietltktals | adrvnninin |
| qgsitfaggp | grdgiidfts | gsellitkak | nghlavvapr |

Insr.

FIG. 2

```
   1   ggagcggggc gccgggtccg gcaggatgcg ctaccgggca tcggccctgg gcagtgacgg
  61   ggttcgagtg accatggaga gcgccttgac tgcccgagac cgggtagggg tgcaggactt
 121   tgtcctgctg gagaatttca ccagtgaggc tgccttcatt gagaacctcc ggcggcggtt
 181   ccgggagaac ctcatttata cctacatcgg tcctgtccta gtctctgtca atccctaccg
 241   agacctacag atctacagcc ggcagcatat ggaacgctac cgtggtgtca gtttctatga
 301   agtaccacct catttgtttg cagtggctga cactgtatac cgggcacttc gtactgagcg
 361   tcgggaccag gcagtgatga tttctggaga gagtggggca ggcaagacag aggccaccaa
 421   gagactgctc cagttctatg cagagacctg cccagcccct gaacggggtg gcgcagtgcg
 481   agaccgcctg ttgcagagca accccgtgtt agaggccttt gggaatgcca agactctccg
 541   caacgataac tccagccggt ttggaaagta catggatgtg cagtttgact tcaagggtgc
 601   ccccgtggga ggccacattc tcagttacct cctggaaaag tcccgggtgg tgcaccaaaa
 661   tcacggagag cggaacttcc acgtcttta ccagctactg gagggggggcg aggaggagac
 721   tctccgtcgg ctgggcttgg aacggaaccc ccagagctac ttgtacctgg tgaagggcca
 781   gtgtgccaag gtctcctcca tcaacgacaa gagtgactgg aaggttatga ggaaggcgct
 841   gtccgtcatt gacttcactg aggatgaagt ggaggacttg ctcagcatcg tggccagcgt
 901   cctacatctg ggcaacatcc actttgctgc tgacgaggac agcaatgccc aggttactac
 961   tgagaaccag ctcaaatatc tgaccaggct ccttggtgtg gaaggtacaa cacttaggga
1021   agccctgacc cacaggaaga tcatcgccaa gggggaagag ctcctgagcc cactgaacct
1081   tgaacaggcg gcatatgcaa gggatgcgct tgccaaggct gtgtacagcc ggacattcac
1141   ctggctggtc agaaagatca ataggtcact ggcctctaag gacgctgaga gccccagctg
1201   gcgaagcacc acggttcttg ggctcctgga catttacggc tttgaagtgt ttcagcataa
1261   cagcttcgag cagttctgca tcaactactg caatgagaag ctgcagcagc tcttcatcga
1321   gctgactctc aagtcggagc aggaggaata cgaggctgag ggcatcgcgt gggaacctgt
1381   ccagtacttc aacaacaaga tcatctgtga cctggtagag gagaagttca agggcatcat
1441   ctccatcttg gatgaagagt gcctgcgtcc tgggggaggcc acggacctga cctttctgga
1501   gaagttggag gacactgtca gccccaccc tcacttcctg acgcacaagc tcgctgacca
1561   gaagaccagg aaatccctag accgagggga gttccgcctt ctgcattatg ctggagaggt
1621   gacctacagt gtgactgggt ttctggataa aaacaatgac ctcctcttcc ggaacctgaa
1681   ggagaccatg tgcagctcaa tgaaccccat catggcccag tgctttgaca agagtgagct
1741   cagtgacaag aagcggccag agacggtggc cacccagttc aagatgagcc tcctgcagct
1801   cgtggagatc ctgaggtcta aggagcctgc ctatatccgg tgcatcaagc aaacgacgc
1861   caagcagccg ggtcgctttg atgaggtgct catccgacat caggtgaagt acctgggact
1921   gatggagaat ctgcgcgtgc gcagagctgg ctttgcctat cgtcgcaaat atgaggcttt
1981   cctgcagagg tacaagtcac tgtgcccaga gacatggccc atgtgggcag acggccccca
2041   ggatggtgtg gccgtgttgg tcagacacct cggctacaag ccagaagagt acaaaatggg
2101   caggactaag atcttcatcc gattccccaa gaccttattt gccacagagg actccctgga
```

FIG. 2 (continued)

```
2161  agtccggcgg cagagtctag ccaccaagat ccaggcggcc tggaggggct ttcattggcg
2221  acagaaattt ctccgggtga agcgatcagc catctgtatc cagtcatggt ggcgtggcac
2281  actgggccgg aggaaggcag ccaagaggaa gtgggcagcc cagaccatcc gtcgactcat
2341  ccgtggcttc attttgcgcc attcaccccg gtgccctgag aatgccttct tcttggacca
2401  cgtgcgcgcc tcattttgc ttaacctgag gcggcaactg ccccggaatg ttctggacac
2461  ctcctggccc acaccccac ctgccctgag agaggcctca gaactgctac gggaactgtg
2521  catgaagaac atggtgtgga agtactgccg gagcatcagc cctgagtgga agcagcagct
2581  gcagcaaaag gcggtggcta gtgaaatttt caagggcaag aaggacaact accccagag
2641  tgtccccaga ctcttcatta gcacacggct tggcacagag gagatcagcc ccagagtgct
2701  tcaatccttg ggctctgaac ccatccagta tgccgtgccc gtggtaaaat acgaccgtaa
2761  gggttacaag cctcgccccc ggcagctgct gctcacgccc agtgctgtgg tcattgtgga
2821  ggatgctaaa gtcaagcaga gaattgatta tgccaaccta accggaatct ctgtcagtag
2881  cctgagtgat agcctatttg tgcttcacgt gcagcgtgaa gacaacaagc agaagggaga
2941  tgtggtgctg cagagtgatc atgtgatcga gacactaacc aagacggccc tcagtgctga
3001  ccgcgtgaac aatatcaaca tcaaccaggg cagcataacg tttgcagggg gtccaggcag
3061  ggacggcatc attgacttca catcgggctc agagcttctc atcaccaagg ctaagaatgg
3121  ccacctggct gtggtggccc cacggctgaa ttctcggtga tgaaggctgc ggtggaccgc
3181  tcctgactcc tgatgcttcc cttagtcccc tcctcccctc cgacttacca aaaactcaag
3241  cttccaaaca gggatccatg gacaccctca aaacccacgc tgcaaactcc tgccttctgc
3301  tcgcccctc ttgaggtgat caggagccag ggagctaccc catgagtggg ccaggccggg
3361  ccacaccaat agaaaagcag aggcctgagc aggccaggcc agccctctgc tgatgccaaa
3421  tatctaagac aagggaattt taactgaggt tttctctgag atttttgat gctttatagg
3481  aaactatttt tttaagaaag ccattttcct accctaaaca cactggatgt gttttccct
3541  gcctcgaaca gggcaaggaa tgtaactgaa agactgactg ggctgggctg gaaggtcctc
3601  ttcttggcca acccttcctt attcccttgt ctgcctgtcc atccacctgc accttttagc
3661  cca
```

Figure 3A

AGCGGGGCGCCGGGTCCGGGCAGG ATG CGC TAC CGG GCA TCG GCC CTG GGC AGT
                                <u>M</u>   R   Y   R   A   S   A   L   G   S
                         ↑ Start site for NMIβ

D   G   V   R   V   T   *M*   E   S   A   L   T   A   R
GAC GGG GTT CGA GTG ACC *ATG* GAG AGC GCC TTG ACT GCC CGA GAC CGG GTA
                            ↑ Consensus MI start site

NUCLEAR MYOSIN I βWITH A 16 AMINO ACID N-TERMINAL EXTENSION

The present invention claims priority from co-pending U.S. Ser. No. 60/214,944 filed Jun. 29, 2000.

The U.S. Government may have rights in the present invention due to partial support provided by NSF MCB 9631833, NSF INT 972416, and NIH HL 59618, NIH GM 37537 and NSF Program ME143.

BACKGROUND OF THE INVENTION

The present invention is directed to a molecular motor actin binding protein, designated Nuclear Myosin Iβ (NMIβ), that includes a 16 amino acid N-terminal extension not present in in other myosin proteins. The 16 amino acid extension is unique to nuclear myosin Iβ and is responsible for the nuclear localization of this protein.

Myosin I is a member of a superfamily of actin binding proteins that hydrolyze adenosine triphosphate (ATP) (Mermall et al., 1998). Most members of this superfamily have been identified based on their DNA sequences. Myosin II is the prototypic member of this family. Myosin II is a two headed, filamentous protein that is an actin-activated ATPase. Myosin II is widely distributed in eukaryotic cells and its role in energy conversion during muscle contraction is well known.

Myosin I is a single headed, non-filamentous, actin-activated ATPase (Pollard and Korn, 1973). First described in *Acanthamoeba castellani* (Pollard and Korn, 1973), myosin I is widely distributed in metazoan cells (Mermall et al., 1998). There are at least four different subclasses of myosin I proteins, all containing a 110–150 kD heavy chain and 1–6 light chains located in the neck region between the head and tail. In vertebrate forms of myosin I, this light chain is calmodulin.

Immunofluorescence studies of mammalian cells have shown that myosin I is diffusely distributed throughout the entire cytoplasm and that it concentrates near cortical surfaces and in the perinuclear region. Although evidence of specific roles of myosin protein in metazoan cells is lacking, it has been suggested, based on localization studies, that myosin I proteins are molecular motors involved in plasma membrane extension, vesicle and organelle and mechanochemical regulation of calcium channels in hair cells (Mermall et al., 1998).

The nucleus contains a filamentous network that is analogous to the cytoskeleton, and nascent DNA has been shown to tightly associate with the nuclear "matrix" (Berezney and Coffey, 1975). Although the composition of this matrix or nucleoskeleton is unclear, it has been suggested that replication of DNA occurs as templates move through replication "factories" anchored to the nucleoskeleton (Cook, 1991). Transcription of ribosomal genes takes place in specific locations in nucleoli known as fibrillar centers. Templates move through an array of RNA polymerases on the surface of those fibrillar centers that are part of a dynamic model of transcription.

Actin is a protein that is abundant in the nucleus (Rando et al., 2000) and is frequently found in association with the nuclear matrix. Actin is reported to associate with small ribonucleoproteins in the processing and transport of RNA. Nuclear-specific actin binding proteins also have been described. Because the injection of anti-actin antibodies into Xenopus oocytes blocks chromosome condensation and the transcription of lampbrush chromosomes (Scheer et al., 1984), actin may be involved in nuclear movements, transcription or other events that require energy. Actin usually works in concert with myosin. Although the presence of myosin II-like proteins in the nucleus has been suggested, these proteins have not been purified or characterized.

Transcription is a process of constructing messenger RNA (mRNA) molecules using a DNA molecule as a template that results in transfer of genetic information to mRNA. Transcription requires energy, and RNA polymerases have been suggested to power the movement of the transcription complexes in a manner analogous to energy conversion by myosin (Yin et al., 1995). However, the precise mechanism and the molecules involved in energy conversion during transcription are not known.

There is a particular need for cellular molecules or molecular structures that can be used to design target pharmaceuticals, as well as a need for the sequences that encode these molecules. Any protein involved in transcription is a site for therapeutic intervention in proliferative disorders.

An actin-based molecular motor of the myosin superfamily is a candidate as an energy conversion molecule involved in transcription.

SUMMARY OF THE INVENTION

The present invention is directed to a protein designated Nuclear Myosin Iβ and the corresponding oligonucleotide sequence. It is a new protein that contains a unique N-terminal sequence, and is a separate gene product that belongs to the myosin Iβ family. The myosin superfamily is composed of at least fourteen members including myosin I and myosin II. The myosin I family includes the myosin Iβ form. Both the known cytoplasmic and the newly discovered nuclear forms of this protein are members of the myosin I subfamily of the myosin superfamily of proteins.

The invention is a myosin-like protein in the nucleus. Special techniques, including the use of a unique antibody and partial denaturation followed by renaturation prior to immunoprecipitation, were used to isolate myosin Iβ, a member of the myosin superfamily, from the nucleus and to show that it is required for transcription.

It was unexpectedly discovered that the 120 kD protein is a new isoform of myosin Iβ that has 98% amino acid sequence homology to the previously known cytoplasmic myosin Iβ, but its functionality is determined by a newly sequenced characteristic 16 amino acid N-terminal extension that is not found in cytoplasmic myosin I.

There has been no previous suggestion of a myosin Iβ protein containing a 16 amino acid N-terminal extension or that this 16 amino acid extension causes nuclear localization of that protein or that myosin Iβ is included in the transcription process.

Figure 1:
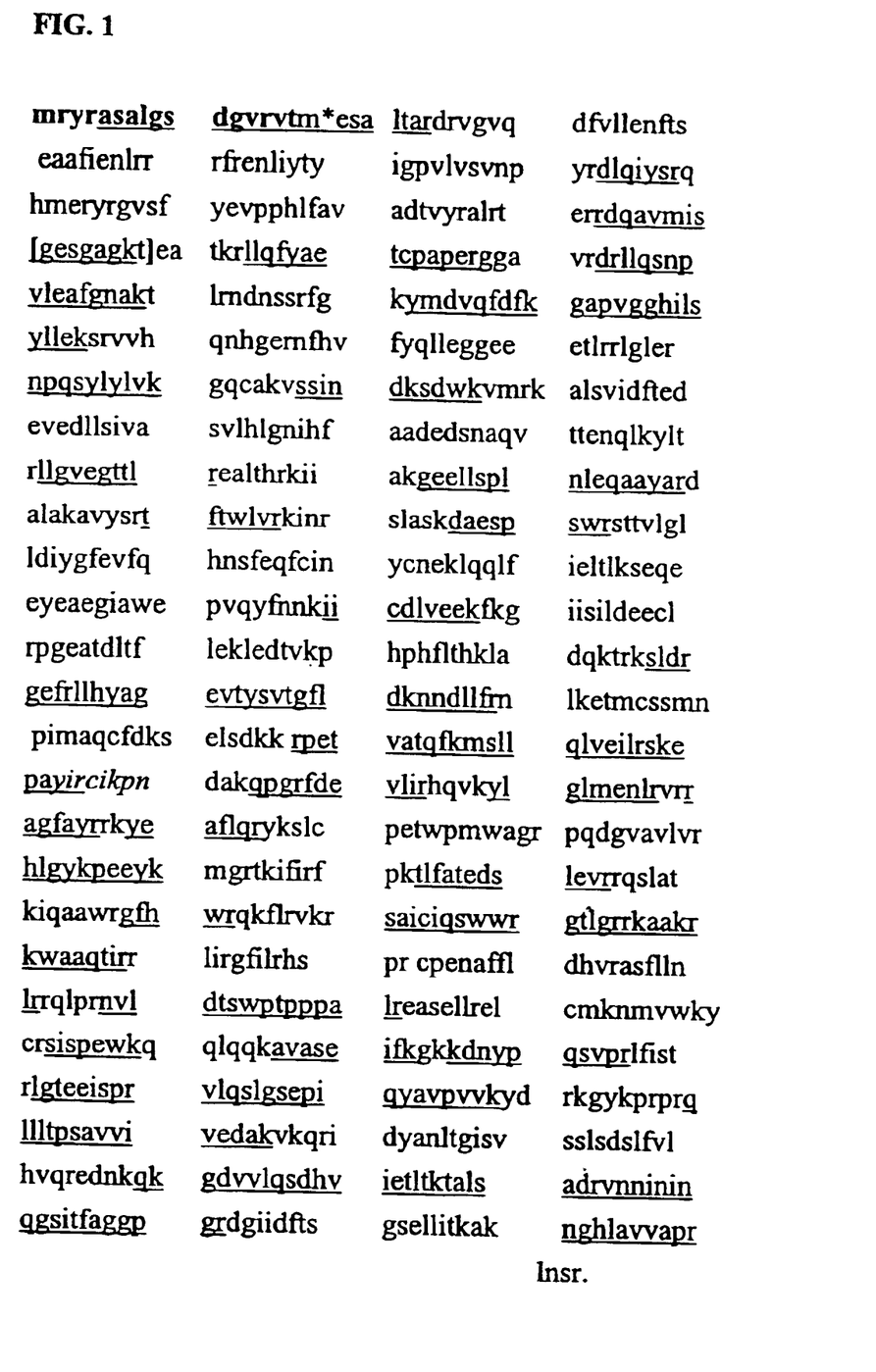
FIG. 1 shows the amino acid sequence of the 120 kD protein of the present invention. The sequence in bold N-terminal to the initiator methionine shows a peptide not present in the known mouse sequences. The new sequence was obtained by microsequencing and 5'-RACE PCR. The consensus ATP binding site is in brackets and the actin binding site is shown in italics. The peptides that were identified by microsequencing are underlined.
Figure 3A:
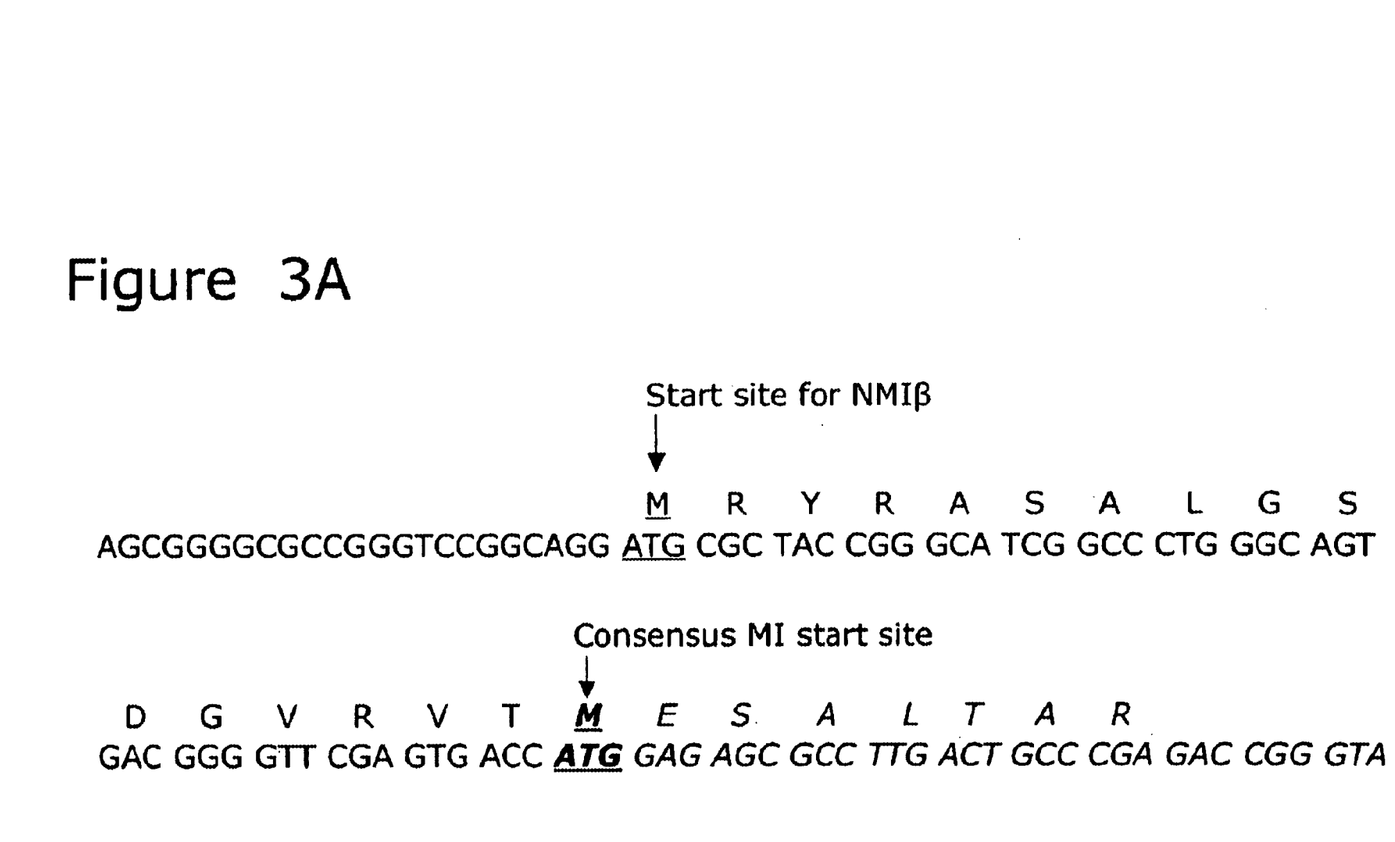
FIG. 3 lists the 5' region of mouse NMIβ cDNA (SEQ ID NO:8) and corresponding amino acid sequence (SEQ ID NO:7) (Panel A) and the organization of the myosin Iβ gene on chromosome 11 (Panel B); in Panel A, the two ATG codons corresponding to the consensus start site and NMIβ start site are underlined; the peptide that overlaps the consensus start site that was obtained by microsequencing (ASALGSDGVRVTMESALTAR)(SEQ ID NO:4) is shown in bold; the previously known mouse myosin Iβ cDNA and protein sequences are in italics.
Figure 3B:
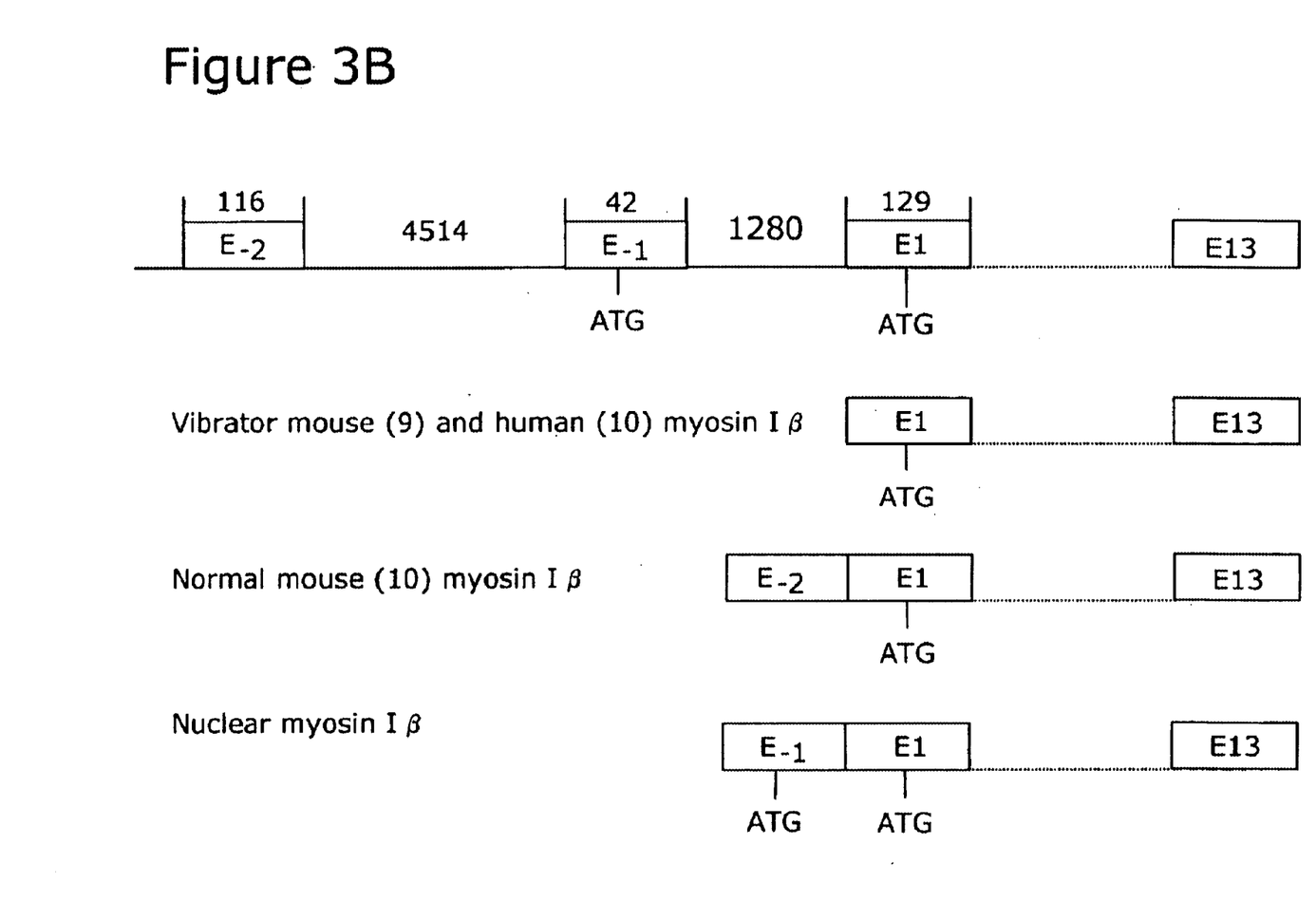

The Nuclear Myosin Iβ protein has an amino acid sequence shown in FIG. 1 (GenBank Accession Number AY 007255). This amino acid sequence includes an initiator methionine and a 16 amino acid peptide N-terminal to the initiator methionine. The peptide includes the amino acid sequence MRYR ASAL GSDG VRVT (SED ID NO:2) at the N-terminal end.

In an embodiment of the present invention, a complementary DNA molecule (cDNA) is synthesized from isolated mRNA's of the Nuclear Myosin Iβ (NMIβ) 16 amino acid N-terminal extension (FIG. 2).

In another embodiment of the present invention, antibodies are directed to the Nuclear Myosin Iβ protein.

Additionally, antibodies directed to the peptide comprising the amino acid sequence MRYR ASAL GSDG VRVT (SED ID NO:2) are produced. The antibodies directed to Nuclear Myosin Iβ protein or to the 16 amino acid peptide as described herein may also be monoclonal antibodies.

In another embodiment of the present invention, electron and confocal microscopy revealed that Nuclear Myosin Iβ co-localizes with RNA polymerase II. RNA polymerase II and Nuclear Myosin I were also shown to co-precipitate, demonstrating that RNA polymerase II and Nuclear Myosin I bind to each other to form a complex.

In another embodiment of the present invention, the Nuclear Myosin Iβ protein forms a functional complex with RNA polymerase II. This complex is actively involved in the transcription process that can be disrupted by inactivating Nuclear Myosin I. The ability to suppress or disrupt the transcription process is useful in designing treatments and gene therapies for conditions wherein cell proliferation should be inhibited.

In an embodiment of the present invention a method is provided for inhibiting cell proliferation. The method comprises the steps of obtaining antibodies to the 16 amino acid N-terminal extension of the Nuclear Myosin Iβ protein and then administering the antibodies to an organism wherein the antibodies contact cells and may inhibit transcription. The antibodies of this method include monoclonal antibodies.

In another embodiment of the present invention, a screening method for inhibiting transcription is disclosed.

DEFINITIONS AND ABBREVIATIONS USED HEREIN

NMIβ=nuclear myosin Iβ.

CMIβ=cytoplasmic myosin Iβ (ie: NMIβ without its characteristic 16 amino acid N-terminal extension).

Molecular motors=molecules that hydrolyze nucleotides and use the energy that is released to do mechanical work at the molecular level. 5'UTR=the untranslated region at the 5 prime end of a nucleotide sequence. 5'RACE=rapid amplification of cDNA ends.

PBS=phosphate buffered saline.

Isoforms=multiple forms of the same protein that differ in their amino acid sequences and are produced by different genes or separate transcripts.

kD=kilodalton.

DTT=dithiothreitol.

EDTA=ethylenediaminetetracetic acid.

EGTA=ethylene glycol-bis(β-amino ethyl ether).

PMSF=phenylmethylsulfonyl fluoride.

BrUTP=5-bromouridine 5'-triphosphate.

ATP=adenosine 5'-triphosphate.

CTP=cytidine 5'-triphosphate.

GTP=guanosine 5'-triphosphate.

UTP=uridine 5'-triphosphate.

The single letter code for amino acids is used herein.

| Amino acid | Three-letter abbreviation | One-letter symbol |
| --- | --- | --- |
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Glutamine | Gln | Q |
| Glutamic acid | Glu | E |
| Glutamine or glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| unknown or other | Xaa | X |

BRIEF DESCRIPTION OF THE DRAWINGS

FIG. 2 shows the oligonucleotide sequence for Nuclear Myosin Iβ.

DETAILED DESCRIPTION OF THE INVENTION

A molecular motor actin binding protein, Nuclear Myosin Iβ, containing a 16 amino acid N-terminal extension, is provided. The protein of the present invention is a molecule with an oligonucleotide sequence coding for Nuclear Myosin Iβ. It is a protein with an estimated molecular weight of 120,000 daltons. Microsequencing of the 120 kD protein and 5' RACE PCR showed that the 120 kD nuclear protein is similar to cytoplasmic myosin Iβ. Surprisingly, the 120 kD protein contained a unique N-terminal extension. This 120 kD protein was named Nuclear Myosin Iβ (NMIβ) to distinguish it from the smaller (116 kD) cytoplasmic myosin Iβ (CMIβ).

As the data from the experiments described herein show, the molecule with an oligonucleotide sequence coding for a Nuclear Myosin Iβ protein contains an ATP binding site, an actin binding site and a unique peptide sequence at the N-terminal to the initiator methionine on cytoplasmic myosin Iβ (CMIβ).

NMIβ is located at sites of actively transcribing genes and it co-localizes with actin in nucleolar structures where ribosomal DNA transcription takes place. The co-localization of actin and Nuclear Myosin Iβ in the same nuclear structure suggests that the NMIβ could power nuclear processes by binding to actin through the actin binding site on the head and negatively charged nuclear components through a conserved, positively charged tail domain. The protein is closely associated with DNA transcription via its interaction with RNA polymerase II. Nuclear Myosin Iβ forms functional complexes with RNA polymerase II. The co-localization of Nuclear Myosin Iβ and RNA polymerase II and the inhibition of RNA synthesis by the anti-NMIβ peptide antibodies suggested that Nuclear Myosin Iβ, perhaps together with RNA polymerases, powers the movement of transcriptional complexes. Transcription is essential for cell proliferation, therefore, any protein that is involved in transcription is a potential target for pharmacological or genetic inhibition of transcription, and consequently of cell proliferation. Because rapid transcription is essential to cell proliferation and cancer is an example of an uncontrolled cell proliferation, Nuclear Myosin Iβ will be useful to the pharmaceutical industry in developing drugs for disease associated with abnormal cell proliferation.

This invention is also directed to purifying antibodies to the NMIβ 16 amino acid N-terminal extension sequence or to an epitope within that sequence, and then administering these antibodies to patients. Given the function of myosin generally as a molecular motor, inactivating NMIβ repressed transcription, possibly by preventing the movement of the RNA polymerase II holoenzyme. Thus, a method for suppressing transcription in proliferating cells would include repressing the expression or function of NMIβ with targeted pharmaceuticals or gene therapy. In particular, the unique 16 amino acid N-terminal and its DNA sequence is useful for designing treatment and gene therapy.

A. Characterization of the Nuclear Myosin I Protein

1. Immunological Studies a. Fluorescence, Confocal and Electron Microscopy

Procedure: Light microscopy was performed on cells growing on coverslips. The cells were fixed in 3% paraformaldehyde in phosphate buffered saline (PBS) and permeabilized with 0.1% deoxycholic acid and 0.1% Triton X-100 in PBS. The cells were then stained with primary antibodies for 2 hrs. at room temperature and visualized using a Texas red, rhodamine or fluorescein conjugated secondary antibodies Coverslips were mounted using Vectashield with DAPI and cells were photographed on a Zeiss Laser confocal microscope.

Electron microscopy was performed on cells grown at 37° C. in suspension in Eagle medium containing 5% fetal bovine serum. Cells were pelleted, fixed in 3% paraformaldehyde plus 0.1% glutaraldehyde in Sörensen buffer, embedded and sectioned using methods known to those of skill in the art. Eighty nanometer thick sections were incubated simultaneously with the rabbit polyclonal antibody to adrenal myosin I (3 μg/ml) and a monoclonal anti-actin antibody (5 μg/ml, Amersham Corporation), washed and incubated with 5 nm gold-conjugated goat anti-mouse antibody and with 10 nm gold-conjugated goat anti-rabbit (British Biocell). After washing, the sections were contrasted for 5 min with a saturated solution of uranyl acetate in water and observed using a Phillips cm. 100 electron microscope.

Results: Epifluorescence and confocal microscopy using the polyclonal antibodies to myosin I showed myosin Iβ staining in the perinuclear region and the leading edges of migrating cells (Nowak et al., 1997). These antibodies also stained the nucleus. Optically sectioning cells through the nucleus demonstrated intranuclear staining.

Electron microscopy demonstrated the presence of immunoreactive material in the cytoplasm and the nucleoplasm of 3T3 cells. (Nowak et al., 1997) Micrographs showed the localization of myosin Iβ antibodies with strong labeling in the nucleoplasm. Moreover, the protein recognized by the myosin Iβ antibody co-localized with actin in the nucleus. High power views through a nucleolus showed that the myosin Iβ antibodies were found mainly in the "dense fibrillar component" where rDNA transcription occurs. These structures surrounded fibrillar centers that contained actin.

b. Western Blot Analysis of Nuclear and Cytoplasmic Fractions

Procedure: Myosin Iβ was purified from bovine adrenal glands as described (Barylko et al., 1992) and then polyclonal antibodies to bovine adrenal myosin I were raised in rabbits using a technique known to those of skill in the art. Specific antibodies were purified from the immune serum on an adrenal myosin Iβ-Sepharose 4B column. Purified adrenal myosin I, whole cell extracts and cytoplasmic and nuclear fractions were separated by SDS-PAGE and transferred to nitrocellulose paper. The nitrocellulose sheets were incubated with affinity-purified polyclonal antibodies to adrenal myosin I (0.4 μg/ml) or mouse monoclonal anti-myosin Iβ antibodies (10 μg/ml) followed by peroxidase-conjugated secondary antibodies.

Results: The well characterized M2 monoclonal antibody to adrenal myosin Iβ (Barylko et al., 1992) cross-reacted with purified adrenal myosin I and a cytoplasmic protein that co-migrated with adrenal myosin I. This protein has a molecular weight of 116 kD. The polyclonal antibodies to adrenal myosin I also recognized purified adrenal myosin I and a 116 kD cytoplasmic protein that co-migrated with adrenal myosin I. In addition, the polyclonal antibodies to adrenal myosin I also recognized proteins with a slightly higher molecular weight (Mr=120,000) in whole cell extracts and nuclear fractions prepared from a number of mammalian cells. The difference in the molecular weight of the myosin Iβ proteins identified by the two antibodies was confirmed by reprobing the nitrocellulose sheets with the complementary antibodies, i.e. first polyclonal antibody and then the monoclonal antibody and vice versa. Thus, the 116 kD protein appeared to be present only in the cytoplasm while the 120 kD protein was found in both the cytoplasm and the nucleus.

2. Determination of the Biochemical Properties of the 120 kD Protein

Procedure: To partially purify the 120 kD protein, the nuclei from about 2 billion cells were isolated using established methods and washed twice by resuspension/centrifugation through a sucrose cushion. The nuclei were resuspended in 1 M NaCl, 1 mM DTT, 0.5% Nonident P-40, 0.4 mM PMSF, 10 μg/ml leupeptin, 10 μg/ml pepstatin, 10 mM $MgCl_2$, 40 mM DNase, 20 mM Tris-HCl, pH 7.5 at 4° C. and extracted by passing through hypodermic needles of decreasing gauge down to a 27 gauge needle. The supernatant was collected by centrifugation (20 mins at 50,000×G), made 10 mM ATP and subjected to ammonium sulfate fractionation. The protein precipitating between 20 and 65% ammonium sulfate was dissolved in 0.5 M NaCl, 1 mM DTT, 5 mM EGTA, 1 mM EDTA, 50 mM Tris-HCl, pH 7.5. ATP and $MgCl_2$ were added to final concentrations of 10 and 12 mM, respectively, the solution was clarified by centrifugation as above and applied to 1.25×70 cm Sepharose 4B gel filtration column.

Fractions containing the 120 kD protein were pooled, concentrated and analyzed to determine if the 120 kD binds actin. The concentrated column fractions were incubated with 0.2 mg/ml F-actin, 50 mM KCl, 1 mM DTT, 1 mM EDTA, 2 mM MgCl$_2$, 1 mM CaCl$_2$, 20 mM Tris-HCl, pH 7.5 (100 μl total) for 60 mins at 4° C. Some samples were made 10 mM ATP, final, and incubated for 10 mins more. All samples were then spun at 100,000×g for 20 mins. The entire pellet and supernatant fractions were analyzed by Western blotting using polyclonal antibodies to myosin Iβ.

Results: Analysis of Sepharose 4B column fractions showed that fractions containing the 120 kD protein, recognized by the polyclonal antibodies described, also contain K$^+$-EDTA ATPase activity. K$^+$-EDTA ATPase activity is a unique feature of myosin molecules that was used to FIRST identify myosin Iβ (Pollard and Korn, 1973). This was the first demonstration of K+-EDTA ATPase activity in the nucleus. The 120 kD protein was also shown to bind actin only when ATP was absent. Because K$^+$-EDTA ATPase activity and actin binding in the absence of ATP are defining features of the myosin superfamily of these data indicated that the 120 kD protein was a member of the myosin superfamily.

3. Positive Identification of the 120 kD Protein

Procedure: Twice washed nuclei (about 40 million) were incubated for 5 min with DFP and then extracted in buffer containing 0.5 mg/ml DNase, 0.2 mg/ml RNase, 1 mM PMSF, 10 μg/ml, each, of aprotinin, leupeptin, pepstatin. The extracts were then centrifuged at 50,000×g for 15 min and 900 μl of the supernatants were combined with 100 μl of 10× immunoprecipitation buffer (50 mM Tris pH 8.0, 150 mM NaCl, 1% Triton, 5 mM EDTA, 1 mM PMSF, 1% SDS) and mixed. Myosin Iβ antibody (20 μg) was added and incubated in a cold room, with shaking, overnight. Protein A-Sepharose (300 μl of 50%) was added and incubated in a cold room for 3 hours. The Sepharose beads were washed extensively with immunoprecipitation buffer and the bound protein was eluted by boiling the Sepharose beads twice in 150 μl of 0.25% SDS, 5 mM DTT, 5 mM Tris at pH 6.8. The eluants were combined, lyophilized and resuspended in 10% sucrose, 0.01% bromophenol blue, 50 mM Tris, pH 6.8. Proteins were separated by SDS PAGE and either stained with Coomassie blue (90% of the immunoprecipitated protein) or subjected to Western blot analysis (remaining 10%) to make sure that the protein used for microsequencing had the correct molecular weight and that it was recognized by the myosin Iβ antibody. Those steps ensured that the correct protein was identified by use. Microsequencing was then performed using the microcapillary HPLC-electrospray ionization-tandem mass spectroscopy method (Hunt et al., 1992). Three rounds of sequencing revealed slightly over 40% of the amino acid sequence.

Results: The state-of-the-art method for identifying a protein is to immunoprecipitate the protein using a specific antibody and to then microsequence the protein. The sequence obtained can then be compared with known protein sequences to positively identify the protein. Therefore, affinity purified antibodies to adrenal myosin I and standard methods were used to immunoprecipitate the 120 kD protein from the nucleus. These initial efforts using non-denaturing conditions to extract nuclei were unsuccessful because the antibodies did not immunoprecipitate the 120 kD protein. Therefore, the nuclear extracts were partially denatured and then renatured before the 120 kD protein was immunoprecipitated.

Using this method, the 120 kD protein was immunoprecipitated from nuclei isolated from NIH 3T3 cells, a mouse fibroblast cell line. SDS page showed the presence of a 120 kD band by Coomassie blue staining. A western blot confirmed that the 120 kD band in the immunoprecipitate was recognized by the myosin Iβ antibody described herein. Microsequencing of the 120 kD Coomassie blue stained band showed that the 120 kD protein has high sequence homology with myosin Iβ showing it to be an isoform of that protein (FIG. 1). It also revealed the presence of a 12 amino acid N-terminal extension that is unique to this protein (FIG. 1).

With the exception of the N-terminal extension, the sequences identified by microsequencing (FIG. 1, underlined) are identical to the amino acid sequence of mouse cytoplasmic myosin Iβ. The NMIβ contains at least part of the consensus ATP (brackets) and actin (italics) binding sites (FIG. 1) because the micro-sequencing overlapped both of these highly conserved sites. In FIG. 1, the consensus start site methionine is identified with an asterisk and the unique peptide is in bold.

The data presented herein demonstrate the following. (a) The presence of a 120-kD protein in nucleus that is recognized by polyclonal antibodies to adrenal myosin Iβ. (b) Immunostaining of the nucleus with affinity-purified polyclonal antibodies to adrenal myosin I. (c) Co-localization of the 120-kD protein and actin in the nucleus. (d) The presence of K$^+$-EDTA ATPase activity in column fractions containing the 120-kD protein following gel filtration chromatography of a nuclear extract. (e) Actin binding by the 120-kD protein only in the absence of ATP. (f) Positive identification of the 120 kD protein as a NMIβ protein; (g) proof NMIβ contains a unique N-terminal extension.

B. Characterization of the cDNA of Nuclear Myosin I

Following the demonstration that the 120 kD protein is a previously undescribed myosin Iβ isoform present in the nucleus, the function of this protein was analyzed. Unexpectedly, a 16 amino acid N-terminal extension was found for that protein that distinguished the sequence from cytoplasmic myosin Iβ. This unique 16 amino acid N-terminal extension has two surprising characteristics. First, it is essential for nuclear localization of the protein. Second, it is involved in transcription when acting with RNA polymerase II.

1. PCR Analysis to Obtain cDNA for the N-Terminal Extension

A 5' RACE was performed using a Mouse Marathon-Ready adapter ligated embryonic mouse cDNA library (Clontech Laboratories, Palo Alto, Calif.). A myosin I primer (5'-CAGGAGGTAACTGAGAATGTGG-3') (SEQ ID NO:6) that anneals 571 bases downstream from the N-terminal end of the gene was used in combination with an AP-1 (adapter primer 5'-CCATCCTAATACGACTCAC TATAGGGC-3') (SEQ ID NO5). PCR was performed using the Advantage cDNA Polymerase mix (Clontech Labs, Palo Alto, Calif.).

Two bands were obtained. One corresponded to the expected 600 base pair fragment and the other to a longer fragment of about 800 base pairs. Cloning and sequencing showed that the smaller band corresponds to the known mouse myosin Iβ. The bigger fragment had an N-terminal extension not previously found in myosin Iβ. Most importantly, 12 of the 16 amino acids in the 5' extension were also present in one of the peptides that was microsequenced (FIG. 2).

In FIG. 2, the two ATG's corresponding to the consensus start site and the predicted NMI start site are underlined. The peptide that overlaps the consensus start site that was obtained by microsequencing (ASALGSDGVRVTMESALTAR) is shown in bold while the known mouse myosin Iβ cDNA and protein sequences are in italics. The primer used for 5' RACE was 571 base pairs downstream of the consensus myosin Iβ start site.

Thus, this new isoform of Myosin Iβ contained a unique 16 amino acid N-terminal extension. This unique 16 amino acid extension at the N-terminus of Nuclear Myosin I differentiates it from Myosin Iβ found in the cytoplasm.

2. Domain Structure of the Mouse Myosin Iβ Gene

The mouse myosin Iβ gene is located in chromosome 11. It is about 12 kb long and contains 13 exons, starting with Exon 1 (Hamilton et al., 1997). The mRNA transcripts obtained from the PCR analysis described above were from the same gene on chromosome 11 for the following reasons. First, none of the mRNA's contained sequences that differ from the myosin Iβ gene on chromosome 11. Second, Fluorescence in Situ Hybridization (FISH) mapped the myosin Iβ gene to a single locus in chromosome 11 (Hasson, et al., 1996). Third, a single cDNA was present in adult rats that contained 2 potential start sites (Ruppert et al., 1995). Although this rat (myr 2) cDNA was very similar to the NMIβ cDNA, only a single protein that starts at the consensus start site was reported (Ruppert et al., 1995).

Analysis of the mouse myosin Iβ gene uncovered 2 additional exons (Exon A and B) located upstream of Exon 1 (Pestic-Dragovich et al., 2000). Initial analysis of the 3' RACE PCR revealed the presence of about 1000 bases in the non-translated region that were not found in the mouse myosin Iβ cDNA's (Hamilton et al., 1997; Crozet et al., 1997). Only about half of these exactly match the 3' UTR of the rat myosin Iβ cDNA (Ruppert et al., 1995).

Although the protein-coding regions of nuclear myosin Iβ cDNA and mouse myosin Iβ were identical, the 5' untranslated regions were quite different. The NMIβ cDNA isolated by 5' RACE PCR from an embryonic mouse library had an unique 5' region. This 42 nucleotide region at the 5' end of the NMIβ mRNA was from Exon B. Exon −1 contained a second translational start codon that was in the same reading frame with the consensus myosin Iβ translational start site on Exon −1. Translation starting from the first ATG on Exon B produced a myosin Iβ with 16 extra amino acids at the N-terminal. Of these, 6 amino acids come from Exon −1 and 10 come from Exon 1. Exon −1 also contributed a stretch of 24 nucleotides, very rich in GC, that constituted the 5' UTR of NMIβ. Therefore, the cytoplasmic and nuclear myosin Iβ isoforms were translated from separate transcripts from the same gene on chromosome 11.

3. Nuclear Localization of the FLAG Epitope

Procedure: The NMIβ and CMIβ cDNA's were cloned into the pCMV-tag vector (Strategene, La Jolla, Calif.) that contained the FLAG epitope. NMIβ cDNA obtained by 5' RACE PCR was cut with EcoR I at the 3' end 9 nucleotides upstream of the stop codon and ligated and cloned into EcoR I cloning site of the pCMV-Tag 4 vector (Stratagene, La Jolla, Calif.). This vector had staggered ends and DNA sequencing was used to determine which of the NMIβ cDNA constructs was in the proper reading frame with the FLAG epitope. Cytoplasmic myosin Iβ (CMIβ) cDNA was also ligated and cloned into pCMV-Tag 4 vector using the same procedure.

3T3 cells growing on coverslips were transfected with 3 μg of FLAG tagged NMIβ or CMIβ cDNA using 10 μl of Lipofectamine reagent (Life Technologies, Rockville, Md). The cells were allowed to grow for 72 hours, fixed in 3% paraformaldehyde and permeabilized with 0.1% deoxycholic acid and 0.1% Triton X-100 in PBS. The cells were then stained with a monoclonal mouse anti-FLAG IgG (Stratagene, La Jolla, Calif.) for 2 hrs at room temperature and visualized using a Texas red conjugated secondary antibody. Coverslips were mounted using Vectashield (Vector Labs, Burlingame, Calif. with DAPI and cells were photographed on Zeiss Laser confocal microscope.

Results: Confocal images of cells lipofected with the NMIβ-FLAG plasmid showed staining of both the nucleus and the cytoplasm. In contrast, the FLAG epitope was confined to the cytoplasm in cells lipofected with the CMIβ-FLAG plasmid. A Z-stack, a three-dimensional image generated using confocal microscopy, confirmed the nuclear localization of the NMIβ-FLAG and cytoplasmic localization of the CMIβ-FLAG. There were two reasons for the nuclear and cytoplasmic staining in cells transfected with the NMIβ-FLAG. First, NMIβ had to be synthesized in the cytoplasm and then transported to the nucleus. Second, the NMIβ cDNA contained start sites for both the NMIβ and CMIβ. Consequently, both proteins, each tagged with the FLAG epitope, were translated and resulted in staining of both the nucleus and the cytoplasm.

Thus, expression of the cDNA for the nuclear isoform of myosin Iβ (NMIβ) resulted in nuclear localization of an epitope tag. In contrast, expression of the shorter myosin Iβ isoform (CMIβ) resulted in cytoplasmic localization of the epitope tag exclusively.

4. Production and Partial Characterization of an Anti-NMIβ Antibody a. Polyclonal Antibodies to NMIβ

Procedure: To produce polyclonal antibodies to the 16 amino acid N-terminal extension of NMIβ, the peptide was synthesized followed by 3 glycine residues and a cysteine residue at the C-terminal end. The glycines residues were used to give rotational freedom to the peptide while the cysteine residue was used to attach the peptide to Keyhole Limpet hemocyanin (KLH), thyroglobulin and bovine serum albumin. Rabbits were immunized with 25 μg, each, of the peptide-KLH conjugate emulsified in complete Freund's adjuvant. The rabbits were boosted 4 weeks later with 25 μg, each, of the peptide-thyroglobulin conjugate emulsified in incomplete Freund's adjuvant. Immunizing rabbits with different conjugates limited the production of antibodies to the carrier. The rabbits were then bled once a week starting 10 days after the boost. All procedures were performed with prior approval from the University of Illinois at Chicago Animal Care Committee and with the supervision of University of Illinois at Chicago Veterinary Staff. Specific, anti-peptide antibodies were purified by applying antisera to an affinity column made by coupling the peptide-BSA conjugate to Sepharose 4B.

Results: For a microscopy evaluation, 3T3 cells were stained with affinity purified anti-NMIβ peptide antibodies or the same antibodies pre-adsorbed with the peptide-KLH conjugate. Confocal microscopy showed that the antibodies stained the cytoplasm and the nucleus, consistent with the idea that the NMIβ is synthesized in the cytoplasm and then transported into the nucleus. Equally importantly, there was no staining when the antibodies were adsorbed with the KLH-NMIβ peptide conjugate. Thus, these data unexpectedly showed that the 16 amino acid extension was responsible for directing the NMIβ to the nucleus.

b. Monoclonal Antibodies

Antibodies that are produced by hybrid cells or hybridomas are called monoclonal antibodies. The hybrid cells are produced by fusing an antibody-secreting cell isolated from an immunized animal with a myeloma cell, which is a type of B-cell tumor. Monoclonal antibodies are powerful reagents for testing for the presence of a desired epitope because all of the antibodies produced by hybridomas detect the same epitope. A technique for production of monoclonal antibodies is known in the art and is described by Harlow et al. (1988). There are three stages to production of monoclonal antibodies. First, the animals must be immunized by injecting the animal with an antigen preparation. Second, a screening procedure must be developed where the sera from test bleeds are used to develop and validate it. Finally, the hybridomas can be produced by first boosting the animals with a sample of the antigen several days prior to fusion. Then, the immunized animal is used to prepare antibody secreting cells which are then mixed with myeloma cells and fused. The cells from positive cells are grown and single-cloned to produce the monoclonal antibodies.

5. Co-Localization of NMIβ and RNA Polymerase II

Procedure: HeLa cells were grown at 37° C. in suspension in Eagle medium containing 5% FBS. The culture was split into three portions and inhibitors of RNA transcription were added to the second (20 μg/ml α-amanitin for 4 hr, 40 min.) and third (0.5 μg/ml actinomycin D for 1 hr) portions. After the desired inhibition time, cells were pelleted, fixed in 3% paraformaldehyde plus 0.1% glutaraldehyde in Sörensen buffer, embedded and sectioned using methods known to those of skill in the art (Pestic-Dragovich et al., 2000). Eighty nanometer thick sections were cut and simultaneously incubated with a monoclonal antibody that recognized the largest subunit of RNA polymerase II (Lavoie et al., 1999) and with the rabbit polyclonal antibody to adrenal myosin I (both 10 μg/ml). The cells were then washed and incubated with 5 nm gold-conjugated goat anti-mouse antibody and with 10 nm gold-conjugated goat anti-rabbit. After washing, the sections were contrasted for 5 min with a saturated solution of uranyl acetate in water Results: Confocal and electron microscopy revealed co-localization of NMIβ and RNA polymerase in control cells (Pestic-Dragovich et al., 2000). The co-localization of NMIβ and RNA polymerase II was lost when cells were treated with α-amanitin, which blocks transcription by stimulating the degradation of the large subunit of RNA polymerase II (Nguyen et al., 1996). The absence of co-localization was shown in two ways: By a reduced density of RNA polymerase II labeling and insignificant co-localization of labels. The co-localization decreased when cells were treated with actinomycin D, which blocks transcription by binding to DNA (Alberts et al., 1994). The decrease was shown by the rarity of the co-localization of RNA polymerase II with NMIβ. When control samples were incubated as above but with one of the primary antibodies omitted, they showed no significant gold labeling.

6. Co-precipitation and In Vitro Transcription Assays.

Procedure: NMIβ was immunoprecipitated from nuclear extracts using affinity purified antibodies to the NMIβ peptide or the same antibodies pre-adsorbed with the peptide. The immunoprecipitates were analyzed by protein immunoblotting using anti-NMIβ peptide antibodies or an antibody to the large subunit of RNA polymerase II (Lavoie et al., 1999).

An in vitro transcription assay that quantifies transcription initiation by RNA polymerase II was performed using a HeLa nuclear extract system as described by the manufacturer (Promega, Madison, Wis.). Nuclear extract (8 units) treated with RNAguard RNase inhibitor (Pharmacia, Piscataway, N.J.) was preincubated with buffer, affinity purified antibodies to smooth muscle myosin II (de Lanerolle et al., 1980), anti-NMI peptide antibody or 0.5 μg α-amanitin (30 mins at room temperature). HeLa cell template DNA (100 ng) containing the cytomegalovirus immediate early promoter was added and the reaction mixture (25 μl) was made with 3 mM MgCl$_2$, 0.4 mM, each, ATP, CTP and UTP. Unlabelled GTP (0.04 mM) and [α$^{32}$P]-labelled GTP (10 μCi) was then added and the reaction mixtures were incubated for 30 mins at 30° C. The transcription products were isolated and separated by 6% acrylamide, 7 M urea denaturing gel electrophoresis and analyzed using a phosphorimager.

Figure 4A:
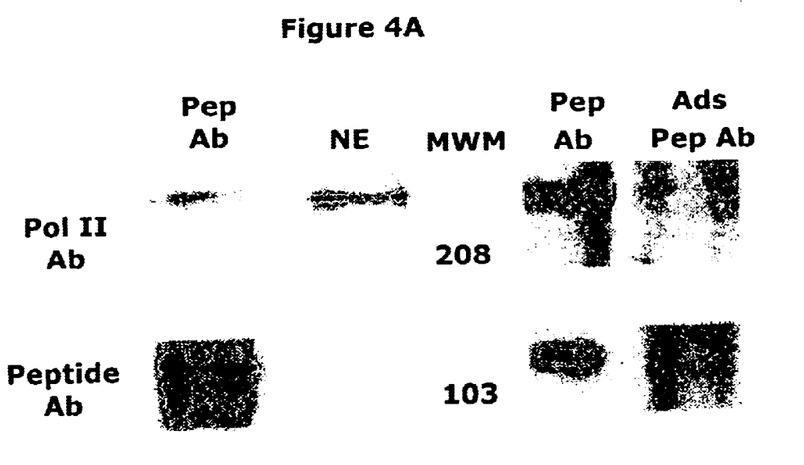
FIG. 4 shows functional association of NMIβ and RNA polymerase II.
Figure 4B:
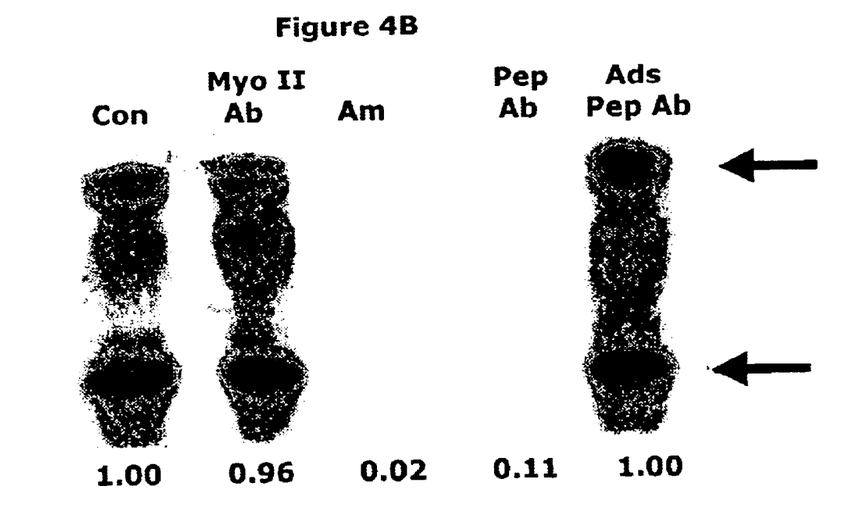

Results: Western blotting revealed the presence of RNA polymerase II in the NMI immunoprecipitate when the blots were probed with an antibody to RNA polymerase II (FIG. 4A). RNA polymerase II was not present in the immunocomplexes when the nuclear myosin Iβ antibody was pre-incubated with the peptide (FIG. 4A). In addition, the anti-NMIβ-peptide antibody inhibited RNA synthesis, in vitro (FIG. 4B). In contrast, neither the same antibodies pre-incubated with peptide nor affinity purified antibodies to myosin II inhibited transcription (FIG. 4B).

7. Methods for Screening for Agents or Procedures that Inhibit NMI Expression or Function.

Because NMI forms a complex with RNA polymerase II and is required for transcription as shown above, agents or procedures that inhibit the expression or functions of NMI could inhibit transcription. A methods for inhibiting NMI expression could include antisensense oligonucleotides (Toulme, 2001). Antisense oligonucleotides have been used over the past 15 years to regulate the expression of specific genes by RNA targeting. The presence of a unique, N-terminal extension in NMI that is not found in other proteins makes NMI an ideal target for antisense oligonucleotides. Oligonucleotide sequences (16 to 20 nucleotides long) that are complementary to the coding region for the unique peptide could be administered to cells. These oligonucleotides could be synthesized by commercial vendors and derivatized, using methods familiar to those skilled in the art, to enhance cellular entry and to enhance binding to RNA. The effects on NMI expression can be monitored by performing western blot analyses or immunofluorescence microscopy, using polyclonal antibodies to adrenal myosin I, polyclonal antipeptide antibodies to NMI or monoclonal antibodies to NMI followed by an appropriate fluorescently-labelled secondary antibody, as described above. The absence of a band that co-migrates with NMI found in nuclear extracts or the absence of nuclear staining by one of these antibodies would provide proof for the suppression of NMI expression.

A method for screening for agents that inhibit NMI function is also of utility. Such agents could include naturally occurring or synthetic compounds, drugs or other formulations that form a complex with NMI and inhibit the translocation of NMI to the nucleus, inhibit the enzymatic activity of NMI and/or the binding of NMI to RNA polymerase II. In such a screening method, cells would be plated on cover slips in media containing 10% calf serum. The cells would then be synchronized by growing them for 24–48 hours in media not containing calf serum, a method familiar to those skilled in the art. The cells would then be stimulated to enter the cell cycle by adding media containing 10% serum and treated with one of the said agents for a period of time. The cells would then be fixed and permeabilized as described above.

Agents that prevent the translocation of NMIβ to the nucleus can be detected by staining cells with using polyclonal antibodies to adrenal myosin I, polyclonal antipeptide antibodies to NMI or monoclonal antibodies to NMIβ followed by an appropriate fluorescently-labelled secondary antibody, as described above. A decrease or an absence of nuclear staining would indicate inhibition of translocation of NMIβ to the nucleus.

Agents or procedures that inhibit NMI translocation or function should also inhibit transcription. To detect inhibition transcription, cells are grown at 60–80% confluency on polylysine or fibronectin coated coverslips so that cells will not be washed away in the permealization step. The cells are rinsed once in glycerol buffer [5 mM $MgCl_2$, 25% glycerol, 0.5 mM PMSF (add fresh), 0.5 mM EGTA, 20 mM Tris-HCl, pH 7.4] at room temperature and permeablized in the glycerol buffer+5 μg/ml digitonin (Calbiochem, La Jalla, Calif.) for 3 mins at room temperature. The permealization buffer is removed and the transcription mixture [100 mM KCl, 5 mM $MgCl_2$, 0.5 mM EGTA, 25% glycerol, 1 mM PMSF (add fresh), 2 mM ATP, 0.5 mM CTP, 0.5 mM GTP, 0.2 mM Br-UTP (Sigma, St. Louis, Mo.), 100 mM, 1 μL/ml RNAsin (add fresh), 50 mM Tris HCl, pH 7.4.] is added. The cells are then incubated at 37 degrees centigrade as desired (7–10 mins). At the end of transcription, the cells are rinsed very gently 2× in PBS and then immediately fixed in 3% freshly made formaldehyde in PBS for 7 mins at room temperature. Cells are then permeabilized with 0.1% deoxycholic acid and 0.1% Triton X-100 in PBS for 7 mins at room temperature and stained with a Alexa Flour-conjugated mouse moloclonal antibody to BrUTP (Molecular Probes, Eugene, Oreg.) for 2 hrs at room. The coverslips are washed and mounted using Vectashield (Vector Labs, Burlingame, Calif.) with DAPI and the cells are examined and photographed with Zeiss Laser confocal microscope using the appropriate filters.

DOCUMENTS CITED

Alberts, B. et al. *The Molecular Biology of the Cell*, 3rd Edition, Garland Publishing Co., New York, 1994, pp. 240.

Barylko, B., Wagner, M. C., Reizes, O. and Albanesi, J. P. Purification and characterization of a mammalian myosin I. *Proc. Natl. Acad. Sci. USA* 89, 490–494, 1992.

Berezney, R. and Coffey, D. S. Nuclear matrix protein: association with newly syn-thesized DNA. *Science* 18, 291–293, 1975.

Cook, P. R. The nucleoskeleton and the topology of replication. *Cell* 66, 627–635, 1991.

Cook, P. R. The organization of replication and transcription. *Science* 284, 1790–1795, 1999.

Crozet, F . . . and Petit, C. Cloning of the genes encoding two murine and human cochlear unconventional type I myosins. *Genomics* 40, 332–341, 1997.

de Lanerolle, P. and Stull, J. T. Myosin phosphorylation during contraction and relaxation of tracheal smooth muscle. *J. Biol. Chem.* 255, 9993–10000, 1980.

Hamilton, B. A. et al. The vibrator mutation causes neurodegeneration via reduced expression of PITP alpha: positional complementation cloning and extragenic suppression. *Neuron* 18, 711–22, 1997

Harlow, E., Lane, D. P. Antibodies: A laboratory manual.139–243, 1988.

Hasson, T., Skowron, J. F., Gilbert, D. J., Avraham, K. B., Perry, W. L., Bement, W. M., Anderson, B. L., Sherr, E. H., Chen, ZY., Green, L. A., Ward, D.C., Corey, D. P., Mooseker, M. S., Copeland, N. G., and Jenkins, N. A. Mapping unconventional myosins in mouse and human. *Genomics* 36, 431–439, 1996.

Hunt, D. L. et al. Characterization of peptides bound to the Class 1 MHC molecule HLA-A2.1 by mass spectroscopy. *Science* 255, 1261–1263, 1992.

Lavoie, S. B., Albert, A. L., Thibodeau A. and Vincent, M. *Biochem Cell Biol.*, 77, 367–74, 1999.

Mermall, V., Post, P. L and Mooseker, M. S. Unconventional myosins in cell movement, membrane traffic and signal transduction. *Science* 279, 527–533, 1998.

Nguyen, V. T., Giannoni, F., Dubois, M. F., Seo, S. J., Vigneron, M., Kédinger, C. and Bensaude, O. In vivo degradation of RNA polymerase II largest subunit triggered by α-amanitin. *Nucleic Acids Res* 24, 15,292-15,929, 1996

Nowak., G., Pestic-Dragovich, L., Hozak, P., Philimonenko, A., Simerly, C., Schatten, G. and de Lanerolle, P. Evidence for the presence of a myosin I like protein in the nucleus. *J.Biol. Chem.* 272, 17,176-17,181, 1997.

Pestic-Dragovich, L., Stojiljkovic, L., Philimonenko, A., Nowak, G., Ke, Y., Settlage, R. E., Shabanowitz, J., Hunt, D. F., Hozak, P. and de Lanerolle, P. A myosin I isoform in the nucleus. *Science* 290: 337–341, 2000

Pollard, T. D. and Korn, E. D. Acanthamoeba myosin I. Isolation from *Acanthaamoeba castellanii* of an enzyme similar to muscle myosin. *J. Biol. Chem.* 248, 4682–4690, 1973.

Rando, O. J., Zhao K. and Crabtree, G. R. *Trends in Cell Biol.* 10, 92–97, 2000.

Ruppert, C., Godel, J., Muller, R. T., Kroschewski, R., Reinhard, J. and Bahler, M. Localization of the rat myosin I molecules myr 1 and myr 2 and in vivo targeting of their tail domains. *J. Cell Sci.* 106, 3775–3786, 1995.

Scheer, U. and Hinssen, H., Franke, W. W. and Jokusch, B. M. Microinjection of actin-binding proteins and actin antibodies demonstrates involvement of nuclear actin in transcription of lampbrush chromosomes. *Cell* 39, 111–122, 1984.

Toulme, J-J. New candidates for true antisense. *Nature Biotechnology* 19, 17–18, 2001.

Yin, H., Wang, M. D., Svoboda, K., Landick, R., Block, S. M. and Gelles, J. Transcription against an applied force. *Science* 270, 1653–1656, 1995.

What is claimed is:

1. An isolated Nuclear Myosin Iβ protein wherein the amino acid sequence comprises:

| | | | |
|---|---|---|---|
| mryrasalgs | dgvrvtmesa | ltardrvgvq | dfvllenfts |
| eaafienlrr | rfrenliyty | igpvlvsvnp | yrdlqiysrq |
| hmeryrgvsf | yevpphlfav | adtvyralrt | errdqavmis |
| gesgagktea | tkrllqfyae | tcpapergga | vrdrllqsnp |
| vleafgnakt | lrndnssrfg | kymdvqfdfk | gapvgghils |
| ylleksrvvh | qnhgernfhv | fyqlleggee | etlrrlgler |
| npqsylylvk | gqcakvssin | dksdwkvmrk | alsvidfted |
| evedllsiva | svlhlgnihf | aadedsnaqv | ttenqlkylt |
| rllgvegttl | realthrkii | akgeellspl | nleqaayard |
| alakavysrt | ftwlvrkinr | slaskdaesp | swrsttvlgl |
| ldiygfevfq | hnsfeqfcin | ycneklqqlf | ieltlkseqe |
| eyeaegiawe | pvqyfnnkii | cdlveekfkg | iisildeecl |
| rpgeatdltf | lekledtvkp | hphflthkla | dqktrksldr |
| gefrllhyag | evtysvtgfl | dknndllfrn | lketmcssmn |
| pimaqcfdks | elsdkkrpet | vatqfkmsll | qlveilrske |
| payircikpn | dakqpgrfde | vlirhqvkyl | glmenlrvrr |
| agfayrrkye | aflqrykslc | petwpmwagr | pqdgvavlvr |
| hlgykpeeyk | mgrtkifirf | pktlfateds | levrrqslat |
| kiqaawrgfh | wrqkflrvkr | saiciqswwr | gtlgrrkaak |
| rkwaaqtirr | lirgfilrhs | prcpenaffl | dhvrasflln |
| lrrqlprnvl | dtswptpppa | lreasellre | lcmknmvwky |
| crsispewkq | qlqqkavase | ifkgkkdnyp | qsvprlfist |
| rlgteeispr | vlqslgsepi | qyavpvvkyd | rkgykprprq |
| llltpsavvi | vedakvkqri | dyanltgisv | sslsdslfvl |
| hvqrednkqk | gdvvlqsdhv | ietltktals | adrvnninin |
| qgsitfaggp | grdgiidfts | gsellitkak | nghlavvapr |
| lnsr (SEQ ID NO:1). | | | |

2. An isolated peptide consisting of an amino acid sequence MRYRASALGSDGVRVT (SEQ ID NO:2.

3. The isolated Nuclear Myosin Iβ protein of claim 1 further comprising an epitope with the amino acid sequence FLAG.

* * * * *

SEQUENCE LISTING

<160> NUMBER OF SEQ ID NOS: 8

<210> SEQ ID NO 1
<211> LENGTH: 1044
<212> TYPE: PRT
<213> ORGANISM: Artificial
<220> FEATURE:
<223> OTHER INFORMATION: Nuclear Myosin 1 beta

<400> SEQUENCE: 1

```
Met Arg Tyr Arg Ala Ser Ala Leu Gly Ser Asp Gly Val Arg Val Thr
1               5                   10                  15

Met Glu Ser Ala Leu Thr Ala Arg Asp Arg Val Gly Val Gln Asp Phe
            20                  25                  30

Val Leu Leu Glu Asn Phe Thr Ser Glu Ala Ala Phe Ile Glu Asn Leu
        35                  40                  45

Arg Arg Arg Phe Arg Glu Asn Leu Ile Tyr Thr Tyr Ile Gly Pro Val
    50                  55                  60

Leu Val Ser Val Asn Pro Tyr Arg Asp Leu Gln Ile Tyr Ser Arg Gln
65                  70                  75                  80

His Met Glu Arg Tyr Arg Gly Val Ser Phe Tyr Glu Val Pro Pro His
                85                  90                  95

Leu Phe Ala Val Ala Asp Thr Val Tyr Arg Ala Leu Arg Thr Glu Arg
            100                 105                 110

Arg Asp Gln Ala Val Met Ile Ser Gly Glu Ser Gly Ala Gly Lys Thr
        115                 120                 125

Glu Ala Thr Lys Arg Leu Leu Gln Phe Tyr Ala Glu Thr Cys Pro Ala
    130                 135                 140

Pro Glu Arg Gly Gly Ala Val Arg Asp Arg Leu Leu Gln Ser Asn Pro
145                 150                 155                 160

Val Leu Glu Ala Phe Gly Asn Ala Lys Thr Leu Arg Asn Asp Asn Ser
                165                 170                 175

Ser Arg Phe Gly Lys Tyr Met Asp Val Gln Phe Asp Phe Lys Gly Ala
            180                 185                 190

Pro Val Gly Gly His Ile Leu Ser Tyr Leu Leu Glu Lys Ser Arg Val
        195                 200                 205

Val His Gln Asn His Gly Glu Arg Asn Phe His Val Phe Tyr Gln Leu
    210                 215                 220

Leu Glu Gly Gly Glu Glu Thr Leu Arg Arg Leu Gly Leu Glu Arg
225                 230                 235                 240

Asn Pro Gln Ser Tyr Leu Tyr Leu Val Lys Gly Gln Cys Ala Lys Val
                245                 250                 255

Ser Ser Ile Asn Asp Lys Ser Asp Trp Lys Val Met Arg Lys Ala Leu
            260                 265                 270

Ser Val Ile Asp Phe Thr Glu Asp Val Glu Asp Leu Leu Ser Ile
        275                 280                 285

Val Ala Ser Val Leu His Leu Gly Asn Ile His Phe Ala Ala Asp Glu
    290                 295                 300

Asp Ser Asn Ala Gln Val Thr Thr Glu Asn Gln Leu Lys Tyr Leu Thr
305                 310                 315                 320

Arg Leu Leu Gly Val Glu Gly Thr Thr Leu Arg Glu Ala Leu Thr His
                325                 330                 335

Arg Lys Ile Ile Ala Lys Gly Glu Glu Leu Leu Ser Pro Leu Asn Leu
            340                 345                 350
```

-continued

```
Glu Gln Ala Ala Tyr Ala Arg Asp Ala Leu Ala Lys Ala Val Tyr Ser
        355                 360                 365

Arg Thr Phe Thr Trp Leu Val Arg Lys Ile Asn Arg Ser Leu Ala Ser
    370                 375                 380

Lys Asp Ala Glu Ser Pro Ser Trp Arg Ser Thr Thr Val Leu Gly Leu
385                 390                 395                 400

Leu Asp Ile Tyr Gly Phe Glu Val Phe Gln His Asn Ser Phe Glu Gln
                405                 410                 415

Phe Cys Ile Asn Tyr Cys Asn Glu Lys Leu Gln Gln Leu Phe Ile Glu
            420                 425                 430

Leu Thr Leu Lys Ser Glu Gln Glu Glu Tyr Glu Ala Glu Gly Ile Ala
            435                 440                 445

Trp Glu Pro Val Gln Tyr Phe Asn Asn Lys Ile Ile Cys Asp Leu Val
        450                 455                 460

Glu Glu Lys Phe Lys Gly Ile Ile Ser Ile Leu Asp Glu Glu Cys Leu
465                 470                 475                 480

Arg Pro Gly Glu Ala Thr Asp Leu Thr Phe Leu Glu Lys Leu Glu Asp
                485                 490                 495

Thr Val Lys Pro His Pro His Phe Leu Thr His Lys Leu Ala Asp Gln
                500                 505                 510

Lys Thr Arg Lys Ser Leu Asp Arg Gly Glu Phe Arg Leu Leu His Tyr
            515                 520                 525

Ala Gly Glu Val Thr Tyr Ser Val Thr Gly Phe Leu Asp Lys Asn Asn
            530                 535                 540

Asp Leu Leu Phe Arg Asn Leu Lys Glu Thr Met Cys Ser Ser Met Asn
545                 550                 555                 560

Pro Ile Met Ala Gln Cys Phe Asp Lys Ser Glu Leu Ser Asp Lys Lys
                565                 570                 575

Arg Pro Glu Thr Val Ala Thr Gln Phe Lys Met Ser Leu Leu Gln Leu
                580                 585                 590

Val Glu Ile Leu Arg Ser Lys Glu Pro Ala Tyr Ile Arg Cys Ile Lys
            595                 600                 605

Pro Asn Asp Ala Lys Gln Pro Gly Arg Phe Asp Glu Val Leu Ile Arg
610                 615                 620

His Gln Val Lys Tyr Leu Gly Leu Met Glu Asn Leu Arg Val Arg Arg
625                 630                 635                 640

Ala Gly Phe Ala Tyr Arg Arg Lys Tyr Glu Ala Phe Leu Gln Arg Tyr
                645                 650                 655

Lys Ser Leu Cys Pro Glu Thr Trp Pro Met Trp Ala Gly Arg Pro Gln
                660                 665                 670

Asp Gly Val Ala Val Leu Val Arg His Leu Gly Tyr Lys Pro Glu Glu
            675                 680                 685

Tyr Lys Met Gly Arg Thr Lys Ile Phe Ile Arg Phe Pro Lys Thr Leu
            690                 695                 700

Phe Ala Thr Glu Asp Ser Leu Glu Val Arg Arg Gln Ser Leu Ala Thr
705                 710                 715                 720

Lys Ile Gln Ala Ala Trp Arg Gly Phe His Trp Arg Gln Lys Phe Leu
                725                 730                 735

Arg Val Lys Arg Ser Ala Ile Cys Ile Gln Ser Trp Trp Arg Gly Thr
            740                 745                 750

Leu Gly Arg Arg Lys Ala Ala Lys Arg Lys Trp Ala Ala Gln Thr Ile
            755                 760                 765
```

-continued

```
Arg Arg Leu Ile Arg Gly Phe Ile Leu Arg His Ser Pro Arg Cys Pro
    770             775             780
Glu Asn Ala Phe Phe Leu Asp His Val Arg Ala Ser Phe Leu Leu Asn
785             790             795             800
Leu Arg Arg Gln Leu Pro Arg Asn Val Leu Asp Thr Ser Trp Pro Thr
            805             810             815
Pro Pro Pro Ala Leu Arg Glu Ala Ser Glu Leu Leu Arg Glu Leu Cys
            820             825             830
Met Lys Asn Met Val Trp Lys Tyr Cys Arg Ser Ile Ser Pro Glu Trp
            835             840             845
Lys Gln Gln Leu Gln Gln Lys Ala Val Ala Ser Glu Ile Phe Lys Gly
    850             855             860
Lys Lys Asp Asn Tyr Pro Gln Ser Val Pro Arg Leu Phe Ile Ser Thr
865             870             875             880
Arg Leu Gly Thr Glu Glu Ile Ser Pro Arg Val Leu Gln Ser Leu Gly
            885             890             895
Ser Glu Pro Ile Gln Tyr Ala Val Pro Val Val Lys Tyr Asp Arg Lys
            900             905             910
Gly Tyr Lys Pro Arg Pro Arg Gln Leu Leu Leu Thr Pro Ser Ala Val
    915             920             925
Val Ile Val Glu Asp Ala Lys Val Lys Gln Arg Ile Asp Tyr Ala Asn
930             935             940
Leu Thr Gly Ile Ser Val Ser Ser Leu Ser Asp Ser Leu Phe Val Leu
945             950             955             960
His Val Gln Arg Glu Asp Asn Lys Gln Lys Gly Asp Val Val Leu Gln
            965             970             975
Ser Asp His Val Ile Glu Thr Leu Thr Lys Thr Ala Leu Ser Ala Asp
            980             985             990
Arg Val Asn Asn Ile Asn Ile Asn  Gln Gly Ser Ile Thr  Phe Ala Gly
    995             1000            1005
Gly Pro Gly Arg Asp Gly Ile  Ile Asp Phe Thr Ser  Gly Ser Glu
    1010            1015            1020
Leu Leu  Ile Thr Lys Ala Lys  Asn Gly His Leu Ala  Val Val Ala
    1025            1030            1035
Pro Arg  Leu Asn Ser Arg
    1040
```

<210> SEQ ID NO 2
<211> LENGTH: 16
<212> TYPE: PRT
<213> ORGANISM: Artificial
<220> FEATURE:
<223> OTHER INFORMATION: N-terminal 16 amino acid extension

<400> SEQUENCE: 2

```
Met Arg Tyr Arg Ala Ser Ala Leu Gly Ser Asp Gly Val Arg Val Thr
1               5                   10                  15
```

<210> SEQ ID NO 3
<211> LENGTH: 3661
<212> TYPE: DNA
<213> ORGANISM: Artificial
<220> FEATURE:
<223> OTHER INFORMATION: NMI Beta

<400> SEQUENCE: 3

```
ggagcggggc gccgggtccg gcaggatgcg ctaccgggca tcggccctgg gcagtgacgg    60
```

-continued

| | |
|---|---|
| ggttcgagtg accatggaga gcgccttgac tgcccgagac cgggtagggg tgcaggactt | 120 |
| tgtcctgctg gagaatttca ccagtgaggc tgccttcatt gagaacctcc ggcggcggtt | 180 |
| ccggagaac ctcatttata cctacatcgg tcctgtccta gtctctgtca atccctaccg | 240 |
| agacctacag atctacagcc ggcagcatat ggaacgctac cgtggtgtca gtttctatga | 300 |
| agtaccacct catttgtttg cagtggctga cactgtatac cggcacttc gtactgagcg | 360 |
| tcgggaccag gcagtgatga tttctggaga gagtggggca ggcaagacag aggccaccaa | 420 |
| gagactgctc cagttctatg cagagacctg cccagcccct gaacgggtg cgcagtgcg | 480 |
| agaccgcctg ttgcagagca accccgtgtt agaggccttt gggaatgcca agactctccg | 540 |
| caacgataac tccagccggt ttggaaagta catggatgtg cagtttgact tcaagggtgc | 600 |
| ccccgtggga ggccacattc tcagttacct cctggaaaag tcccgggtgg tgcaccaaaa | 660 |
| tcacggagag cggaacttcc acgtcttta ccagctactg gaggggggcg aggaggagac | 720 |
| tctccgtcgg ctgggcttgg aacgaaccc ccagagctac ttgtacctgg tgaagggcca | 780 |
| gtgtgccaag gtctcctcca tcaacgacaa gagtgactgg aaggttatga ggaaggcgct | 840 |
| gtccgtcatt gacttcactg aggatgaagt ggaggacttg ctcagcatcg tggccagcgt | 900 |
| cctacatctg ggcaacatcc actttgctgc tgacgaggac agcaatgccc aggttactac | 960 |
| tgagaaccag ctcaaatatc tgaccaggct ccttggtgtg aaggtacaa cacttaggga | 1020 |
| agccctgacc cacaggaaga tcatcgccaa ggggaagag ctcctgagcc cactgaacct | 1080 |
| tgaacaggcg gcatatgcaa gggatgcgct tgccaaggct gtgtacagcc ggacattcac | 1140 |
| ctggctggtc agaaagatca ataggtcact ggcctctaag gacgctgaga gccccagctg | 1200 |
| gcgaagcacc acggttcttg ggctcctgga catttacggc tttgaagtgt tcagcataa | 1260 |
| cagcttcgag cagttctgca tcaactactg caatgagaag ctgcagcagc tcttcatcga | 1320 |
| gctgactctc aagtcggagc aggaggaata cgaggctgag ggcatcgcgt gggaacctgt | 1380 |
| ccagtacttc aacaacaaga tcatctgtga cctggtagag gagaagttca agggcatcat | 1440 |
| ctccatcttg gatgaagagt gcctgcgtcc tggggaggcc acggacctga cctttctgga | 1500 |
| gaagttggag gacactgtca gccccaccc tcacttcctg acgcacaagc tcgctgacca | 1560 |
| gaagaccagg aaatccctag accgagggga gttccgcctt ctgcattatg ctggagaggt | 1620 |
| gacctacagt gtgactgggt tctggataa aaacaatgac ctcctcttcc ggaacctgaa | 1680 |
| ggagaccatg tgcagctcaa tgaacccat catggcccag tgctttgaca agtgagct | 1740 |
| cagtgacaag aagcggccag acggtggcc acccagttca agatgagcct cctgcagctc | 1800 |
| gtggagatcc tgaggtctaa ggagcctgcc tatatccggt gcatcaagcc aaacgacgcc | 1860 |
| aagcagccgg gtcgctttga tgaggtgctc atccgacatc aggtgaagta cctgggactg | 1920 |
| atggagaatc tgcgcgtgcg cagagctggc tttgcctatc gtcgcaaata tgaggctttc | 1980 |
| ctgcagaggt acaagtcact gtgcccagag acatggccca tgtgggcagg acggccccag | 2040 |
| gatggtgtgg ccgtgttggt cagacacctc ggctacaagc cagaagagta caaaatgggc | 2100 |
| aggactaaga tcttcatccg attccccaag accttatttg ccacagagga ctccctggaa | 2160 |
| gtccggcggc agagtctagc caccaagatc caggcggcct ggaggggctt tcattggcga | 2220 |
| cagaaatttc tccgggtgaa gcgatcagcc atctgtatcc agtcatgtg gcgtggcaca | 2280 |
| ctgggccgga ggaaggcagc caagaggaag tgggcagccc agaccatccg tcgactcatc | 2340 |
| cgtggcttca ttttgcgcca ttcacccccg tgccctgaga atgccttctt cttggaccac | 2400 |
| gtgcgcgcct catttttgct taacctgagg cggcaactgc cccggaatgt tctggacacc | 2460 |

-continued

```
tcctggccca cacccccacc tgccctgaga gaggcctcag aactgctacg ggaactgtgc    2520
atgaagaaca tggtgtggaa gtactgccgg agcatcagcc ctgagtggaa gcagcagctg    2580
cagcaaaagg cggtggctag tgaaattttc aagggcaaga aggacaacta cccccagagt    2640
gtccccagac tcttcattag cacacggctt ggcacagagg agatcagccc cagagtgctt    2700
caatccttgg gctctgaacc catccagtat gccgtgcccg tggtaaaata cgaccgtaag    2760
ggttacaagc ctcgcccccg gcagctgctg ctcacgccca gtgctgtggt cattgtggag    2820
gatgctaaag tcaagcagag aattgattat gccaacctaa ccggaatctc tgtcagtagc    2880
ctgagtgata gcctatttgt gcttcacgtg cagcgtgaag acaacaagca aagggagat    2940 gtggtgctgc agagtgatca tgtgatcgag acactaacca agacggccct cagtgctgac    3000
cgcgtgaaca atatcaacat caaccagggc agcataacgt ttgcaggggg tccaggcagg    3060
gacggcatca ttgacttcac atcgggctca gagcttctca tcaccaaggc taagaatggc    3120
cacctggctg tggtggcccc acggctgaat tctcggtgat gaaggctgcg gtggaccgct    3180
cctgactcct gatgcttccc ttagtcccct cctcccctcc gacttaccaa aaactcaagc    3240
ttccaaacag ggatccatgg acaccctcaa aacccacgct gcaaactcct gccttctgct    3300
cgccccctct tgaggtgatc aggagccagg gagctacccc atgagtgggc caggccgggc    3360
cacaccaata gaaaagcaga ggcctgagca ggccaggcca gccctctgct gatgccaaat    3420
atctaagaca agggaatttt aactgaggtt ttctctgaga tttttgatg ctttatagga    3480 aactattttt ttaagaaagc cattttccta ccctaaacac actggatgtg ttttcccctg    3540
cctcgaacag ggcaaggaat gtaactgaaa gactgactgg gctgggctgg aaggtcctct    3600
tcttggccaa cccttcctta ttcccttgtc tgcctgtcca tccacctgca ccttttagcc    3660
a                                                                    3661
```

<210> SEQ ID NO 4
<211> LENGTH: 20
<212> TYPE: PRT
<213> ORGANISM: Artificial
<220> FEATURE:
<223> OTHER INFORMATION: NMI Beta Peptide Overlapping Consensus Start Site

<400> SEQUENCE: 4

Ala Ser Ala Leu Gly Ser Asp Gly Val Arg Val Thr Met Glu Ser Ala
1               5                   10                  15

Leu Thr Ala Arg
        20

<210> SEQ ID NO 5
<211> LENGTH: 22
<212> TYPE: DNA
<213> ORGANISM: Artificial
<220> FEATURE:
<223> OTHER INFORMATION: Myosin I primer

<400> SEQUENCE: 5
caggaggtaa ctgagaatgt gg                                              22

<210> SEQ ID NO 6
<211> LENGTH: 27
<212> TYPE: DNA
<213> ORGANISM: Artificial
<220> FEATURE:
<223> OTHER INFORMATION: Adapter primer

```
<400> SEQUENCE: 6
ccatcctaat acgactcact atagggc                                        27

<210> SEQ ID NO 7
<211> LENGTH: 24
<212> TYPE: PRT
<213> ORGANISM: Artificial
<220> FEATURE:
<223> OTHER INFORMATION: peptide encoded by 5' region of mouse NMI Beta cdna

<400> SEQUENCE: 7

Met Arg Tyr Arg Ala Ser Ala Leu Gly Ser Asp Gly Val Arg Val Thr
1               5                   10                  15

Met Glu Ser Ala Leu Thr Ala Arg
            20

<210> SEQ ID NO 8
<211> LENGTH: 104
<212> TYPE: DNA
<213> ORGANISM: Artificial
<220> FEATURE:
<223> OTHER INFORMATION: 5' region of mouse NMI Beta cdna

<400> SEQUENCE: 8
agcggggcgc cgggtccggc aggatgcgct accgggcatc ggccctgggc agtgacgggg    60
ttcgagtgac catggagagc gccttgactg cccgagaccg ggta                   104
```